US00PP31924P3

(12) United States Plant Patent
van den Haak

(10) Patent No.: US PP31,924 P3
(45) Date of Patent: Jun. 30, 2020

(54) ***PHLOX* PLANT NAMED 'IFPHLFRS'**

(50) Latin Name: *Phlox paniculata*
Varietal Denomination: IFPHLFRS

(71) Applicant: Jelle van den Haak, Amsterdam (NL)

(72) Inventor: Jelle van den Haak, Amsterdam (NL)

(73) Assignee: Innoflora Plant Breeding B.V., Heerhugowaard (NL)

( * ) Notice: Subject to any disclaimer, the term of this patent is extended or adjusted under 35 U.S.C. 154(b) by 0 days.

(21) Appl. No.: 16/501,194

(22) Filed: Mar. 5, 2019

(65) Prior Publication Data

US 2020/0053935 P1 Feb. 13, 2020

Related U.S. Application Data

(60) Provisional application No. 62/764,553, filed on Aug. 7, 2018.

(51) Int. Cl.
*A01H 5/02* (2018.01)
*A01H 6/70* (2018.01)

(52) U.S. Cl.
USPC ..... Plt./320
CPC ..... *A01H 6/70* (2018.05)

(58) Field of Classification Search
USPC ..... Plt./320
See application file for complete search history.

*Primary Examiner* — Susan McCormick Ewoldt
(74) *Attorney, Agent, or Firm* — C. A. Whealy

(57) ABSTRACT

A new and distinct cultivar of *Phlox* plant named 'IFPHLFRS', characterized by its compact and uniformly mounded plant habit; moderately vigorous to vigorous growth habit; freely branching habit; dark green-colored leaves; freely flowering habit; flowers that are light red purple in color with darker red purple-colored throats; and good container and garden performance.

2 Drawing Sheets

Botanical designation: *Phlox paniculata.*
Cultivar denomination: 'IFPHLFRS'.

CROSS-REFERENCED TO CLOSELY RELATED APPLICATIONS

Title: Varieties of *Phlox* Plants
Applicant: Jelle van den Haak
Provisional application Ser. No. 62/764,553
Filed: Aug. 7, 2018

BACKGROUND OF THE INVENTION

The present invention relates to a new and distinct cultivar of *Phlox* plant, botanically known as *Phlox paniculata*, typically grown as a container and garden *Phlox*, hereinafter referred to by the name 'IFPHLFRS' and disclosed in U.S. Provisional Patent Application Ser. No. 62/764,553.

The new *Phlox* plant is a product of a planned breeding program conducted by the Inventor in Andijk, The Netherlands. The objective of the breeding program is to create new vigorous *Phlox* plants with numerous attractive flowers.

The new *Phlox* plant originated from a cross-pollination of an unnamed proprietary selection of *Phlox paniculata* as the female, or seed, parent with an unnamed proprietary selection of *Phlox paniculata* as the male, or pollen, parent. The new *Phlox* plant was discovered and selected as a single plant from within the progeny of the stated cross-pollination in a controlled nursery environment in Andijk, The Netherlands in July, 2011.

Asexual reproduction of the new *Phlox* plant by cuttings in a controlled environment in Andijk, The Netherlands since September, 2017 has shown that the unique features of this new *Phlox* plant are stable and reproduced true to type in successive generations.

SUMMARY OF THE INVENTION

The new *Phlox* plant has not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'IFPHLFRS'. These characteristics in combination distinguish 'IFPHLFRS' as a new and distinct *Phlox* plant:

1. Compact and uniformly mounded plant habit.
2. Moderately vigorous to vigorous growth habit.
3. Freely branching habit.
4. Dark green-colored leaves.
5. Freely flowering habit.
6. Flowers that are light red purple in color with darker red purple-colored throats.
7. Good container and garden performance.

Plants of the new *Phlox* and the parent selections differ primarily in plant and growth habit as plants of the new *Phlox* are more uniform and more vigorous than plants of the parent selections.

Plants of the new *Phlox* can also be compared to plants of *Phlox paniculata* Bartwelve, disclosed in U.S. Plant Pat. No. 11,804. In side-by-side comparisons, plants of the new *Phlox* and Bartwelve differ in the following characteristics:

1. Plants of the new *Phlox* have larger flowers than plants of Bartwelve.
2. Plants of the new *Phlox* and Bartwelve differ in flower color as flowers of plants of the new *Phlox* are light red purple in color with darker red purple-colored throats whereas flowers of plants Bartwelve are light purple in color.

BRIEF DESCRIPTION OF THE PHOTOGRAPHS

The accompanying photographs illustrate the overall appearance of the new *Phlox* plant showing the colors as true as it is reasonably possible to obtain in colored reproductions of this type. Colors in the photographs may differ slightly from the color values cited in the detailed botanical description which accurately describe the colors of the new *Phlox* plant.

The photograph on the first sheet is a side perspective view of a typical flowering plant of 'IFPHLFRS' grown in a container.

The photographs on the second sheet are close-up views of a typical inflorescence (upper photograph) and typical leaves (lower photograph) of 'IFPHLFRS'.

DETAILED BOTANICAL DESCRIPTION

The aforementioned photographs and following observations and measurements describe plants grown during the summer in 17-cm containers in an outdoor nursery in Heerhugowaard, The Netherlands and under cultural practices typically used in commercial *Phlox* production. During the production of the plants, day temperatures ranged from 10° C. to 25° C. and night temperatures ranged from 4° C. to 15° C. Plants were pinched five weeks after planting and were 15 weeks old when the photographs and description were taken. In the following description, color references are made to The Royal Horticultural Society Colour Chart, 2015 Edition, except where general terms of ordinary dictionary significance are used.

Botanical classification: *Phlox paniculata* 'IFPHLFRS'.

Parentage:

*Female, or seed, parent.*—Unnamed proprietary selection of *Phlox paniculata*, not patented.

*Male, or pollen, parent.*—Unnamed proprietary selection of *Phlox paniculata*, not patented.

Propagation:

*Type.*—By terminal cuttings.

*Time to initiate roots, summer.*—About 12 days at temperatures about 20° C.

*Time to initiate roots, winter.*—About 16 days at temperatures about 20° C.

*Time to produce a rooted young plant, summer.*—About 36 days at temperatures about 18° C.

*Time to produce a rooted young plant, winter.*—About 42 days at temperatures about 18° C.

*Root description.*—Medium in thickness, moderately fibrous; close to 158B to 158C in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Herbaceous perennial; broadly upright and compact plant habit; overall shape, roughly globular; moderately vigorous to vigorous in growth habit and moderate growth rate.

*Plant height, soil level to top of foliar plane.*—About 20.8 cm.

*Plant height, soil level to top of floral plane.*—About 26 cm.

*Plant width (spread).*—About 37.6 cm.

*Lateral branches.*—Quantity: Typically three primary branches and about 15 secondary branches per plant. Length: About 14.1 cm. Diameter: About 3 mm. Internode length: About 2.4 cm. Strength: Strong. Aspect: Upright to about 40° from vertical. Texture and luster: Sparsely pubescent; moderately glossy. Color: Close to N77A; color becoming closer to 144A with development.

Leaf description:

*Arrangement.*—Opposite, simple.

*Length.*—About 7 cm.

*Width.*—About 2.9 cm.

*Shape.*—Elliptic to slightly ovate or obovate; slightly carinate.

*Apex.*—Apiculate.

*Base.*—Obtuse to attenuate.

*Margin.*—Entire; very finely serrate, serrations are inconspicious.

*Texture and luster, upper and lower surfaces.*—Smooth, glabrous; slightly rugose; matte.

*Venation pattern.*—Pinnate.

*Color.*—Developing leaves, upper and lower surfaces: Close to 145A. Fully expanded leaves, upper surface: Close to NN137B; venation, close to 144A. Fully expanded leaves, lower surface: Close to 191A; venation, close to 144B.

*Petioles.*—Length: About 2.5 mm. Diameter: About 2 mm by 3 mm. Texture and luster, upper and lower surfaces: Smooth, glabrous; matte. Color, upper surface: Close to 146B. Color, lower surface: Close to 144B.

Flower description:

*Flower type and flowering habit.*—Single rotate and salverform flowers arranged in compound terminal panicles; flowers face upright to outwardly; panicles roughly hemispherical in shape; freely flowering habit with about 160 flowers developing per inflorescence and about 2,400 flowers developing per plant during the flowering season.

*Fragrance.*—Moderately fragrant; sweet, pleasant.

*Natural flowering season.*—Plants begin flowering about 15 weeks after planting; long flowering period, plants flower continuously throughout the summer in The Netherlands.

*Flower longevity.*—Flowers last about ten days on the plant; flowers not persistent.

*Flower buds.*—Height: About 2.8 cm. Diameter: About 4 mm. Shape: Oblanceolate. Texture and luster: Smooth, glabrous; slightly glossy. Color: Close to 73A; tube, close to N77B; developing calyx, close to 145B tinged with close to N199A.

*Inflorescence height.*—About 11.2 cm.

*Inflorescence diameter.*—About 11.2 cm.

*Flower diameter.*—About 3.2 cm.

*Flower depth.*—About 2.6 cm.

*Flower throat diameter.*—About 3 mm.

*Flower tube length.*—About 2.1 cm.

*Flower tube diameter.*—About 3 mm.

*Petals.*—Quantity per flower: Typically five in a single whorl; petals fused at the base into a narrow tube; free parts slightly imbricate. Length (including tube): About 3.5 cm; 60% of the petal is fused. Lobe width: About 1.3 cm. Lobe shape: Spatulate. Lobe apex: Obtuse. Margin: Entire; slightly undulate. Texture and luster, upper surface: Smooth, glabrous; velvety; matte. Texture and luster, lower surface: Smooth, glabrous; slightly velvety; slightly glossy. Texture, throat: Smooth, glabrous; moderately velvety. Texture, tube: Densely pubescent. Color: When opening, upper surface: Close to 68B. When opening, lower surface: Close to 73B. Fully opened, upper surface: Between 63B and 73B; venation, similar to lamina colors; color does not change with development. Fully opened, lower surface: Close to 73A to 73C; venation, similar to lamina colors; color does not change with development. Throat: Close to 61B; venation, close to 61B. Tube: Close to 77B; venation, close to 77B.

*Sepals.*—Quantity per flower: Typically five in a single whorl, fused towards the base; calyx, campanulate. Length: About 8 mm; 50% of the sepal is fused. Width: About 1.5 mm. Shape: Lanceolate. Apex: Narrowly apiculate. Margin: Entire; not undulate. Texture and luster, upper surface: Smooth, glabrous; slightly glossy. Texture and luster, lower surface: Moderately pubescent; slightly glossy. Color: When opening, upper surface: Close to 145C tinged with close to N199A; towards the margins, close to 186D. When opening, lower surface: Close to 145B tinged with close to N199A; towards the margins, close to 186D. Fully opened, upper surface: Close to 145B tinged with close to N199A; towards the margins, close to 186D; venation, close to N199A. Fully opened, lower surface: Close to 145A tinged with close to N199A; towards the margins, close to 186D; venation, close to N199A.

*Peduncles.*—Length, terminal peduncles: About 6.3 cm. Diameter, terminal peduncles: About 3 mm. Aspect, primary peduncles: Erect. Aspect, secondary peduncles: About 45° from vertical. Strength: Strong. Texture and luster: Moderately pubescent; matte. Color: Close to 144A.

*Pedicels.*—Length: About 4 mm. Diameter: About 1 mm. Angle: About 20° from the peduncle axis. Strength: Moderately strong. Texture and luster: Moderately pubescent; moderately glossy. Color: Close to 144B.

*Reproductive organs.*—Stamens: Quantity per flower: Typically five. Filament length: About 1 mm. Filament color: Close to N155A. Anther size: About 1.75 mm by 1 mm. Anther shape: Narrowly oblong. Anther color: Close to 158D. Pollen amount: Moderate. Pollen color: Close to 11D. Pistils: Quantity per flower: One. Pistil length: About 1.5 cm. Style length: About 1.3 cm. Style color: Close to 146D. Stigma size: About 1.5 mm by 2 mm. Stigma shape: Cleft, three-parted. Stigma color: Close to 150D. Ovary color: Close to 143B.

*Seeds and fruits.*—To date, seed and fruit development have not been observed on plants of the new *Phlox*.

Garden performance: Plants of the new *Phlox* have been observed to have good garden performance and tolerate rain, wind, high temperatures about 35° C. and to be suitable for USDA Hardiness Zones 6 through 10.

Pathogen & pest resistance: Plants of the new *Phlox* have been not been observed to be resistant to pathogens and pests common to *Phlox* plants.

It is claimed:

1. A new and distinct *Phlox* plant named 'IFPHLFRS' as illustrated and described.

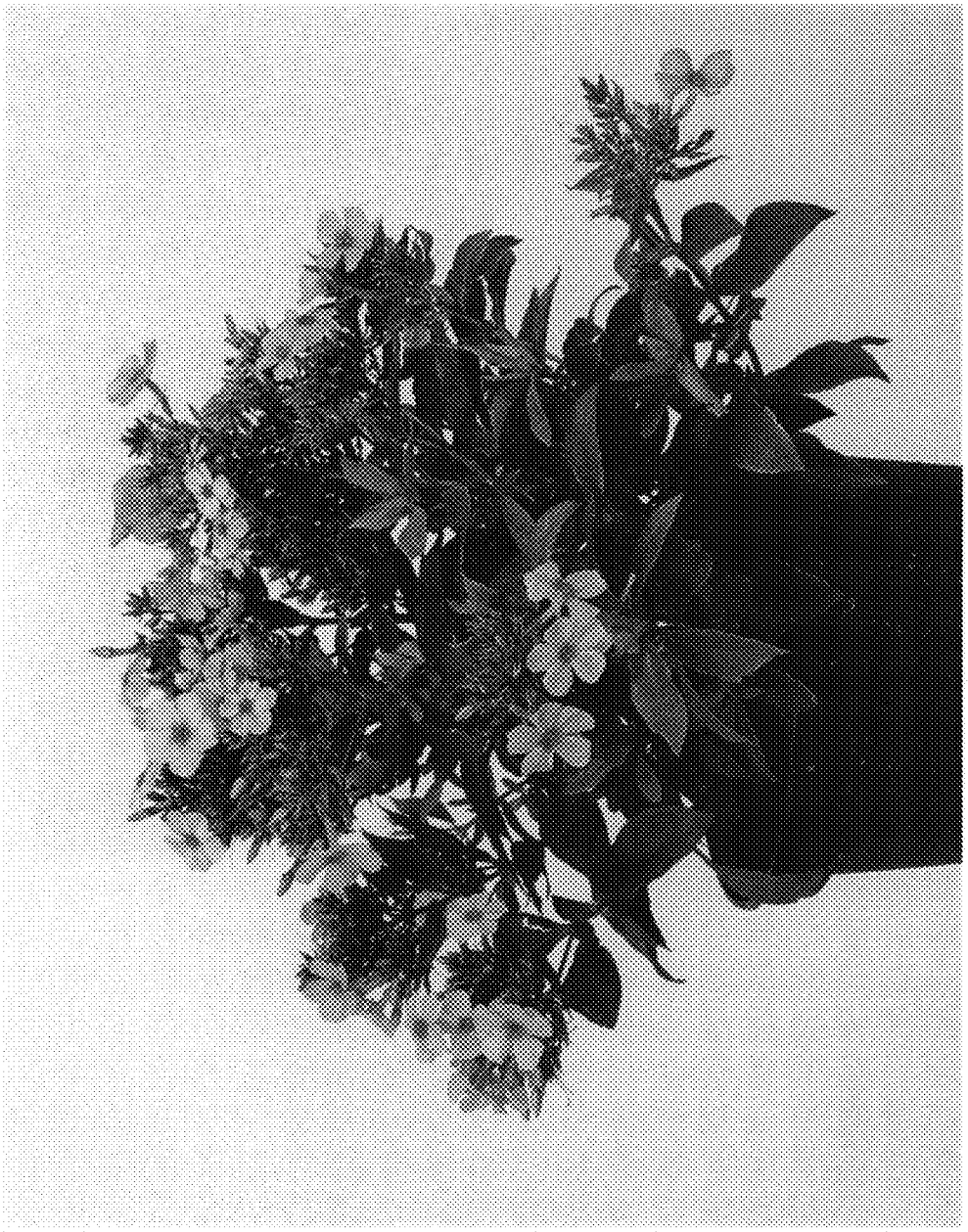

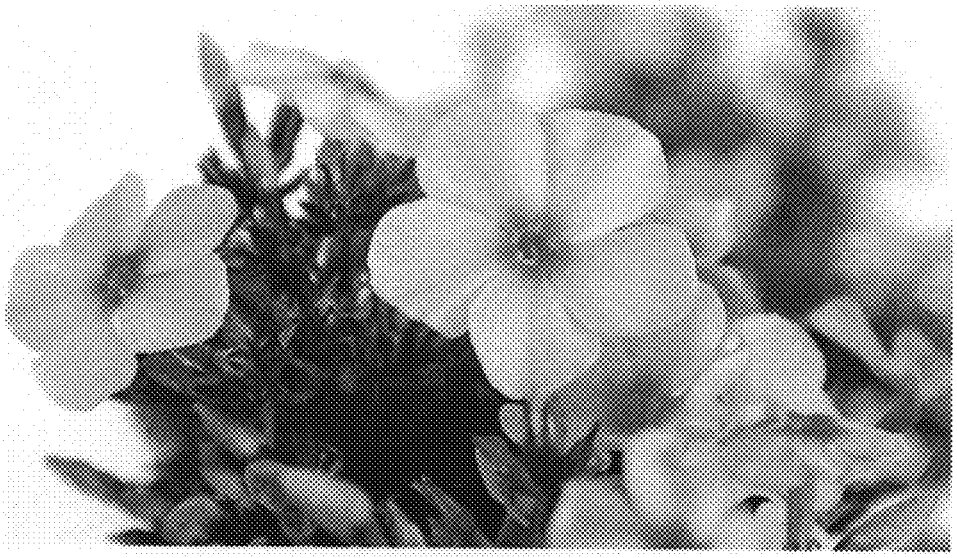
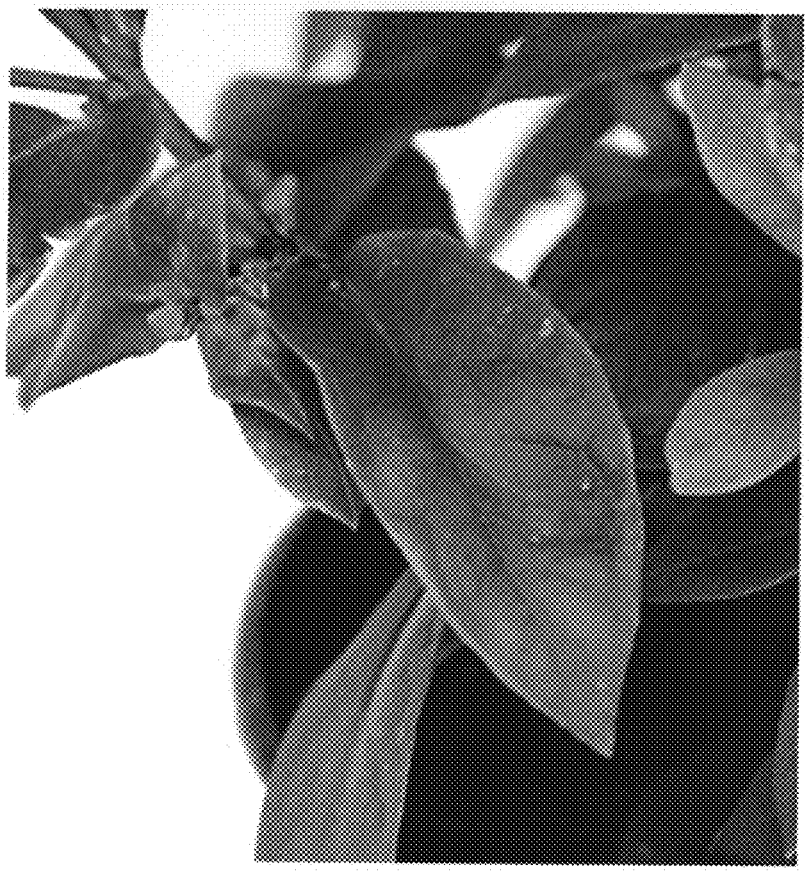

* * * * *